United States Patent [19]

Effland et al.

[11] Patent Number: 5,177,088
[45] Date of Patent: Jan. 5, 1993

[54] SUBSTITUTED 3-(PYRIDINYLAMINO)-INDOLES

[75] Inventors: Richard C. Effland; Joseph T. Klein, both of Bridgewater; Lawrence L. Martin, Lebanon, all of N.J.

[73] Assignee: Hoechst-Roussel Pharmaceuticals Incorporated, Somerville, N.J.

[21] Appl. No.: 688,964

[22] Filed: Apr. 17, 1991

[51] Int. Cl.$^5$ .................... A61K 31/44; C07D 401/12
[52] U.S. Cl. .................... 514/339; 514/318; 514/212; 514/235.2; 514/255; 546/273; 546/193; 546/194; 546/147; 546/274; 546/271; 540/597; 544/131; 544/124; 544/360
[58] Field of Search ............. 546/273; 514/339

[56] References Cited

U.S. PATENT DOCUMENTS 4,970,218 11/1990 Effland et al. ............ 546/273

FOREIGN PATENT DOCUMENTS 0224830 6/1987 European Pat. Off. .

OTHER PUBLICATIONS

Kwartler, J. Amer. Chem. Soc., 65, 1804–1806 (1943).
Vivona, J. Heterocyclic Chem., 16, 783–784 (1979).

"Indoles", Part II edited by J. Houlihan, Chapter VI, pp. 210–212 Wiley-Interscience (1972).

Primary Examiner—Jane T. Fan
Attorney, Agent, or Firm—Tatsuya Ikeda

[57] ABSTRACT

There are disclosed various compounds of the formula below,

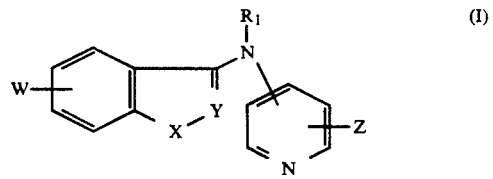

where $R_1$, W, X, Y and Z are as defined in the specification; which are useful for alleviating various memory dysfunctions such as Alzheimer's disease, as modulators of neurotransmitter function such as serotonergic and adrenergic, and as such are useful as antidepressants, anxiolytics, atypical antipsychotics, antiemetics, and for the treatment of personality disorders such as obsessive compulsive disorders.

15 Claims, No Drawings

SUBSTITUTED 3-(PYRIDINYLAMINO)-INDOLES

The present invention relates to compounds of the formula,

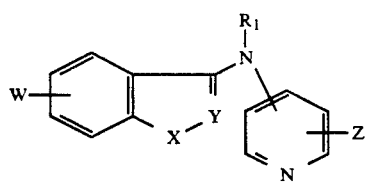

where
R$_1$ is hydrogen, loweralkyl, loweralkenyl, loweralkynyl, arylloweralkyl, aminoloweralkyl, loweralkylaminoloweralkyl, formyl, loweralkylcarbonyl, aminoloweralkylcarbonyl or loweralkoxycarbonyl; the group —X—Y= is

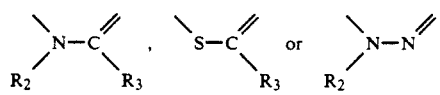

R$_2$ and R$_3$ being independently hydrogen or loweralkyl;
W is hydrogen, halogen, hydroxy, loweralkoxy, arylloweralkoxy or

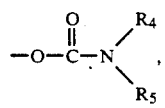

where R$_4$ is hydrogen, loweralkyl or arylloweralkyl; R$_5$ is loweralkyl or arylloweralkyl; or alternatively the group

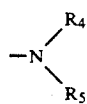

as a whole is

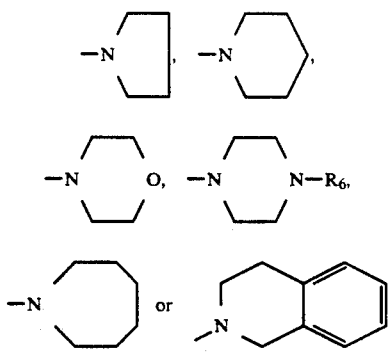

, R$_6$ being hydrogen, loweralkyl, aryl or arylloweralkyl; and Z is hydrogen, halogen, loweralkyl, nitro or amino; which are useful for alleviating various memory dysfunctions such as Alzheimer's disease, as modulators of neurotransmitter function such as serotonergic and adrenergic, and as such are useful as antidepressants, anxiolytics, atypical antipsychotics, antiemetics, and for the treatment of personality disorders such as obsessive compulsive disorders.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group substituted with 0, 1 or 2 substituents each of which being independently loweralkyl, loweralkoxy, halogen or trifluoromethyl.

Throughout the specification and the appended claims, a given chemical formula or name shall encompass all stereo, optical and tautomeric isomers where such isomers exist.

The compounds of this invention are prepared by utilizing one or more of the synthetic steps described below.

Throughout the description of the synthetic steps, the notations R$_1$ through R$_6$ and W, X, Y and Z shall have the respective meanings given above unless otherwise stated or indicated and other notations shall have their respective meanings as defined in their first appearances.

The starting 3-aminoindoles of Formula II can be prepared by methods known to the art, for instance, by utilizing reduction of 3-nitrosoindoles with Na$_2$S$_2$O$_4$. See in this regard, "Indoles", Part II, edited by W. J. Houlihan, Wiley-Interscience, New York, 1972 and European Patent Application 0,224,830 (1987).

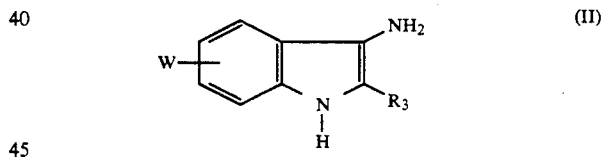

The staring 3-aminobenzo[b]thiophenes of Formula III can also be prepared by methods known to the art. The reader is referred, for instance, to D. E. Boswell et al., J. Heterocyclic Chem., 5, 69 (1968), and Heilbron, "Dictionary of Organic Compounds", p. 151.

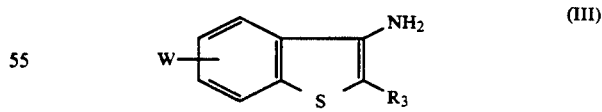

The starting 3-aminoindazoles of Formula IV can also be prepared by methods known to the art.

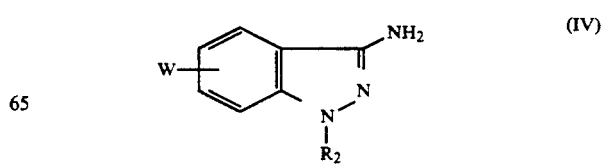

Thus, for instance, Virona et al., J. Heterocyclic Chem., 16, 783 (1989) disclose the reaction depicted below in which $R_2$ is hydrogen or methyl.

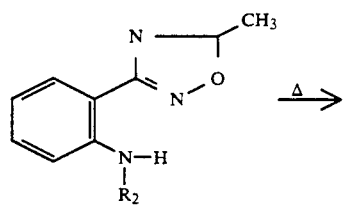

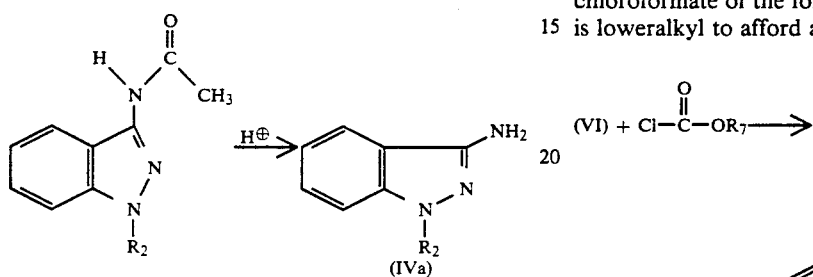

STEP A

Compound II is allowed to react with a chloropyridine hydrochloride of Formula V to afford a compound of Formula VI.

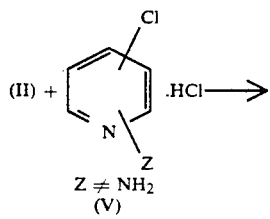

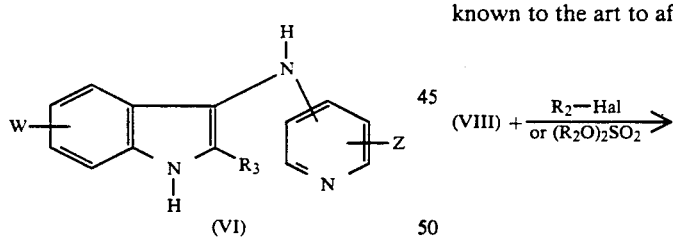

Said reaction is typically conducted in an ethereal solvent such as bis(2-methoxyethyl)ether, diethyl ether, dimethoxyethane, dioxane or tetrahydrofuran or polar aprotic solvent such as dimethylformamide, dimethylacetamide, N-methyl-2-pyrrolidone, hexamethylphosphoramide or dimethylsulfoxide or protic solvent such as ethanol or isopropanol at a temperature of between about 20° C. and 150° C.

Similary, compound III is allowed to react with compound V in substantially the same manner as above to afford a compound of Formula VII.

(III) + (V) ⟶

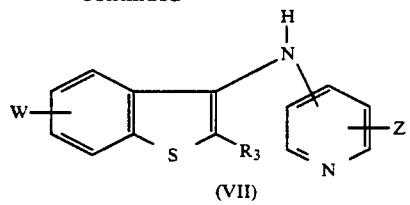

STEP B

Compound VI is allowed to react with a loweralkyl chloroformate of the formula Cl—CO—$OR_7$ where $R_7$ is loweralkyl to afford a compound of formula VIII.

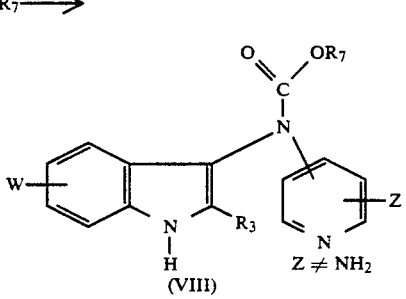

Said reaction is conducted typically in a suitable solvent such as dichloromethane in the presence of a suitable base such as sodium bicarbonate or triethylamine at a temperature of about 20°–60° C.

STEP C

Compound VIII is allowed to react with a loweralkyl halide of the formula $R_2$-Hal where $R_2$ is loweralkyl and Hal is chlorine or bromine, or with a diloweralkyl sulfate of the formula $(R_2O)_2SO_2$ in a routine manner known to the art to afford a compound of Formula IX.

$$(VIII) + \xrightarrow{R_2\text{—Hal} \atop \text{or } (R_2O)_2SO_2}$$

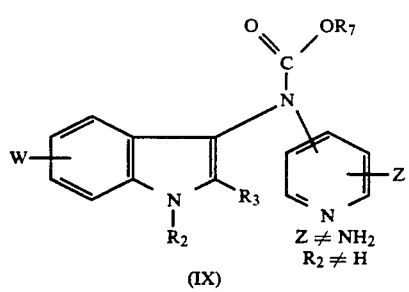

Said reaction is conducted typically in a suitable solvent such as dimethylformamide or tetrahydrofuran in the presence of a suitable base such as sodium or potassium hydride or potassium-t-butoxide at a temperature of about 0°–120° C.

STEP D

Compound IX is hydrolyzed to afford a compound of formula X.

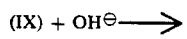

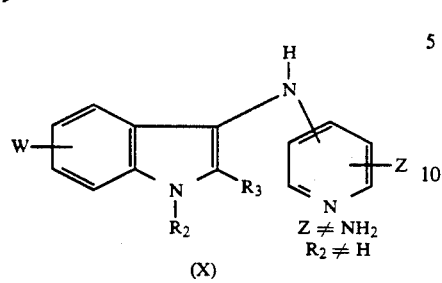

Said hydrolysis is conducted typically by stirring a mixture comprising compound IX, an alkali hydroxide such as sodium hydroxide and a suitable medium such as ethanol or other loweralkanol plus water at a temperature of about 20°-100° C.

STEP E

Compound X is allowed to react with a halide compound of the formula $R_8$—Hal, where $R_8$ is loweralkyl, loweralkenyl, loweralkynyl or arylloweralkyl, at a temperature of about −10° C.-80° C., preferably between 0° C.-25° C. to afford a compound of Formula XI.

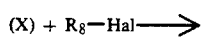

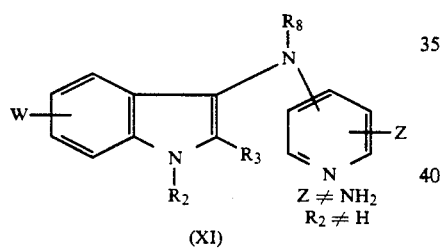

Said reaction is conducted typically in a suitable solvent such as dimethylformamide, dimethylsulfoxide, ethereal solvents or aromatic hydrocarbon in the presence of a suitable base such as sodium or potassium hydride or potassium-t-butoxide.

Compound X is allowed to react with a compound of the formula

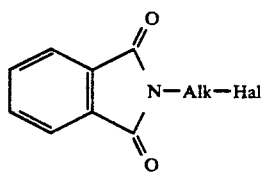

where "Alk" is a loweralkylene group and Hal is Cl or Br and in a routine manner known to the art to afford a compound of Formula XII. Thereafter, Compound XII is treated with hydrazine or methylamine in a routine manner known to the art to afford a compound of Formula XIII.

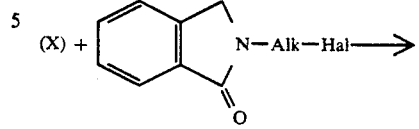

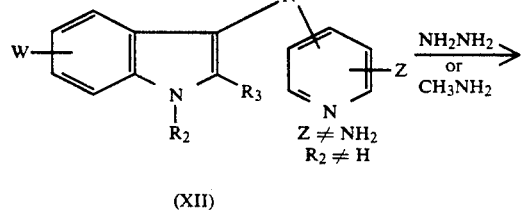

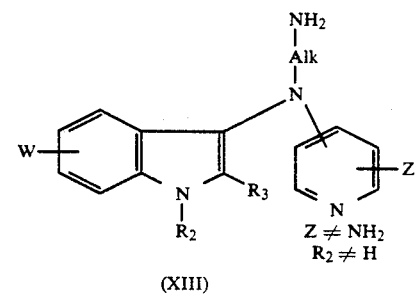

Compound X is allowed to react with a dihalolower-alkane of the formula Hal-Alk-Hal in a routine manner known to the art to afford a compound of Formula XIV and thereafter the latter is allowed to react with a compound of the formula $R'NH_2$, where $R'$ is hydrogen or loweralkyl in a routine manner known to the art to afford a compound of the Formula XV.

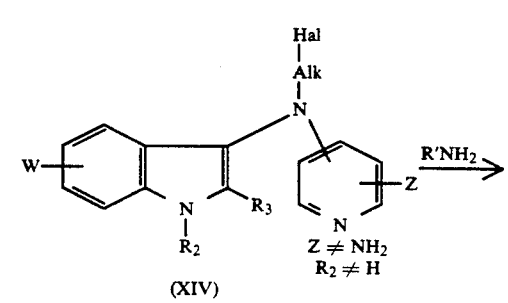

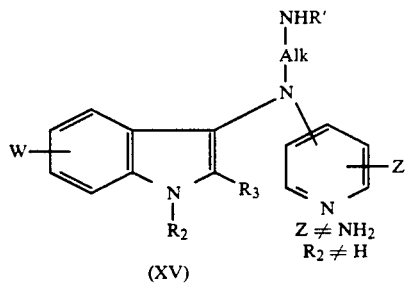

(XV)

STEP F

Compound X (where $R_2$ may be hydrogen, corresponding to Compound VI) is allowed to react with an acid halide of the formula

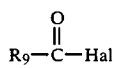

where $R_9$ is loweralkyl, in a routine manner known to the art to afford a compound of Formula XVI.

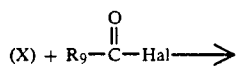

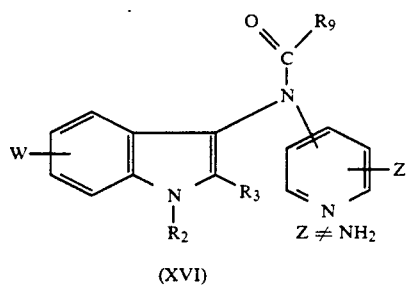

(XVI)

Alternatively to the above, where $R_9$ is hydrogen or loweralkyl, an acid anhydride of the formula, $R_9$—CO—O—CO—$R_9$ may be used in a routine manner known to the art to accomplish the same purpose.

Compound X is allowed to react with a compound of formula

where R is t-butyl or benzyl in a routine manner know to the art to afford a compound of Formula XVII and thereafter the latter is hydrolyzed or subjected to catalytic hydrogenolysis in a routine manner known to the art to afford a compound of the Formula XVIII.

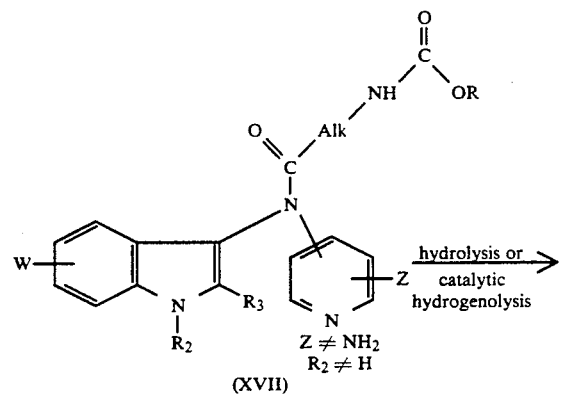

(XVII)

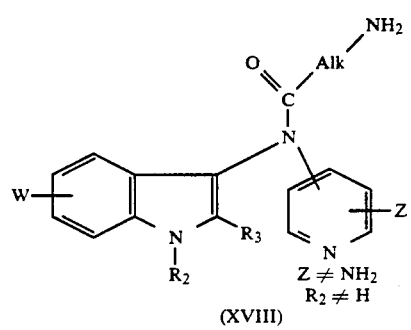

(XVIII)

Alternatively to the above, Compound X is allowed to react with a carboxylic acid of Formula XIX in the presence of dicyclohexylcarbodiimide to afford Compound XVII.

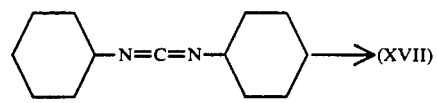

STEP G

Compound XVIa obtained from STEP F is reduced with LiAlH$_4$ or other suitable reducing reagent in a routine manner known to the art to afford a compound of Formula XX.

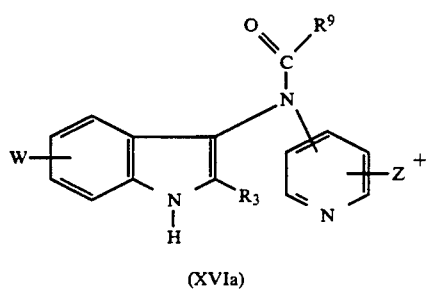

(XVIa)

-continued

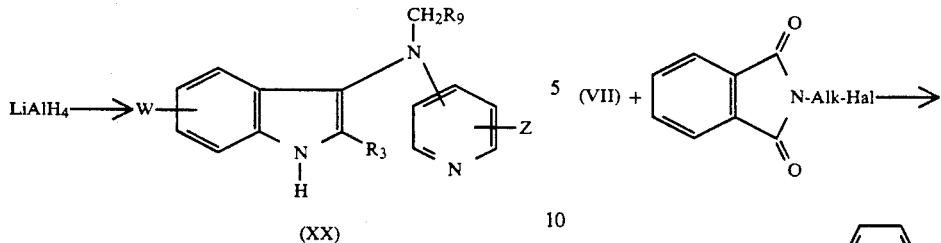

(XX)

STEP H

Compound VII is allowed to react with a loweralkyl chloroformate of the formula $Cl-CO-OR_7$ in substantially the same manner as in STEP B to afford a compound of Formula XXI.

(VII) + Cl—C(=O)—OR$_7$ ⟶

(XXI)   $Z \neq NH_2$

STEP I

Compound VII is allowed to react with a halide compound of the formula $R_8$-Hal in substantially the same manner as in STEP E to afford a compound of Formula XXII.

(VII) + R$_8$-Hal ⟶

(XXII)

Compound VII is allowed to react with a compound of the formula

N-alk-Hal (phthalimide)

to afford a compound of Formula XXIII and thereafter the product is treated with hydrazine or methylamine in substantially the same manner as in STEP E to afford a compound of Formula XXIV.

(VII) + (phthalimide N-Alk-Hal) ⟶

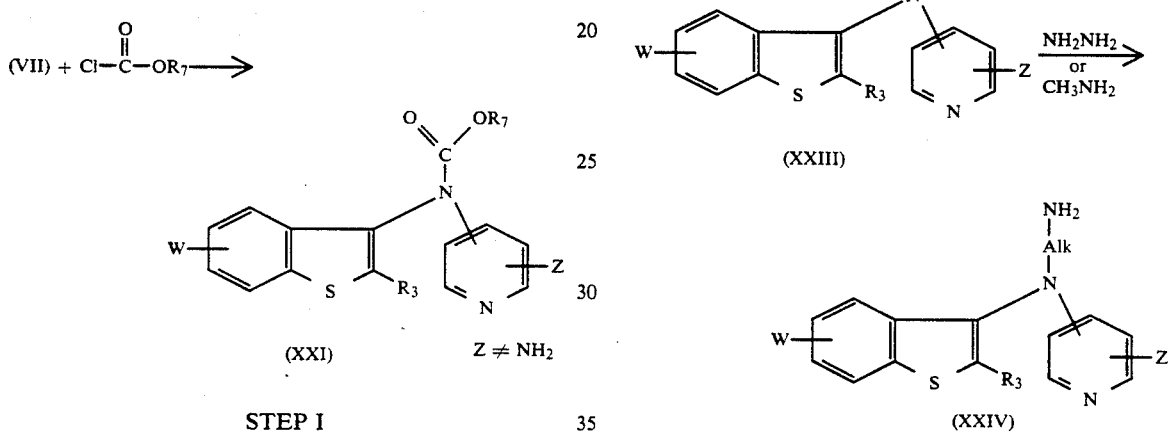

(XXIII) →[$NH_2NH_2$ or $CH_3NH_2$]

(XXIV)

Compound VII is allowed to react with compound of the formula Hal-Alk-Hal to afford a compound of Formula XXV and the product is allowed to react with a compound of the formula $R'NH_2$ in substantially the same manner as in STEP E to afford compound of Formula XXVI.

(VII) + Hal—Alk—Hal ⟶

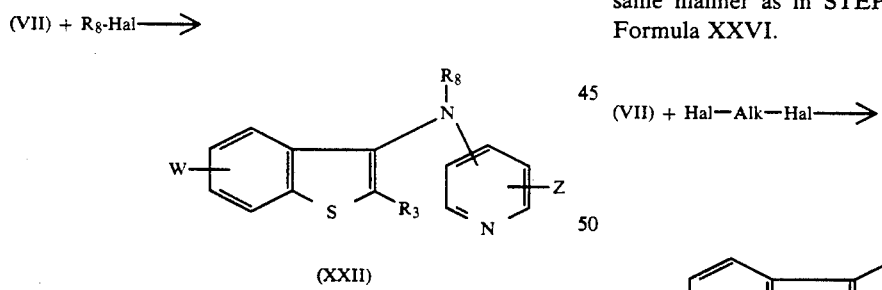

(XXV) →[$R'NH_2$]

(XXVI)

STEP J

Compound VII is allowed to react with an acid halide of the formula

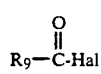

in substantially the same manner as in STEP F to afford a compound of Formula XXVII.

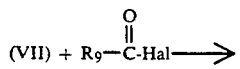

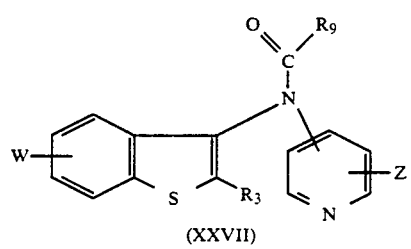

(XXVII)

Compound VII is allowed to react with a compound of the formula $$RO-\overset{O}{\underset{\|}{C}}-NH\text{-Alk-}\overset{O}{\underset{\|}{C}}\text{-Hal}$$

to afford a compound of Formula XXVIII and thereafter the product is hydrolyzed or subjected to catalytic hydrogenolysis in substantially the same manner as in STEP F to afford a compound of Formula XXIX.

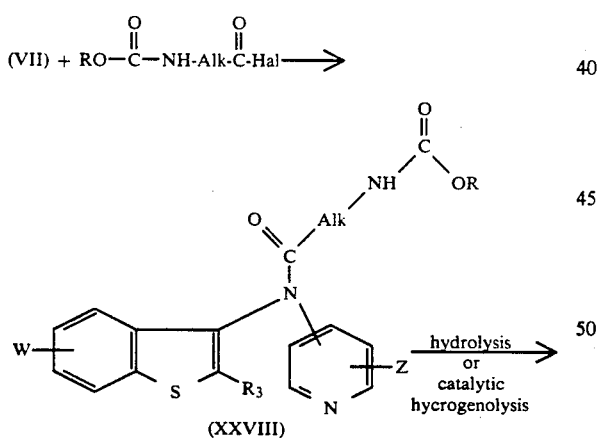

Compound VII is allowed to react with compound XIX in the presence of dicyclohexylcarbodiimide in substantially the same manner as in STEP F to afford compound XXVIII.

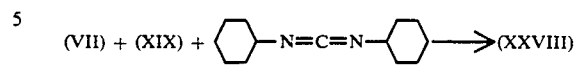

STEP K

Compound IV is allowed to react with Compound V in substantially the same manner as in STEP A to afford a compound of formula XXX.

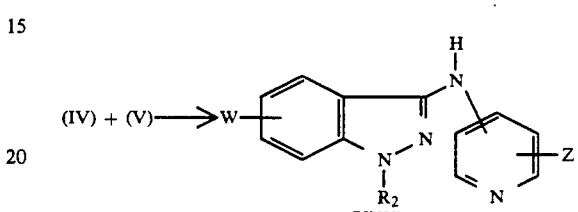

STEP L

Compound XXX is allowed to react with a loweralkyl chloroformate of the formula Cl—CO—OR$_7$ in substantially the same manner as in STEP B to afford a compound of formula XXXI.

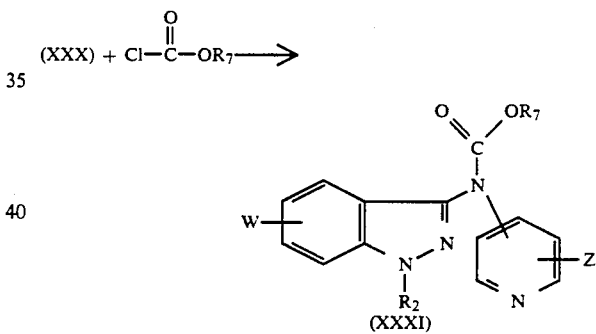

STEP M

Compound XXX is allowed to react with a halide compound of the formula R$_8$-Hal in substantially the same manner as in STEP E to afford a compound of Formula XXXII.

(XXX) + R$_8$-Hal ⟶

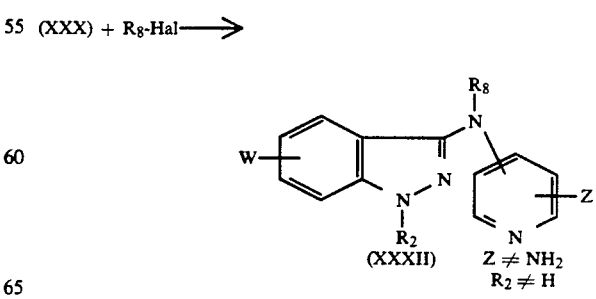

Compound XXX is allowed to react with a compound of the formula

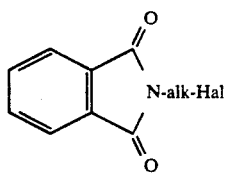

to afford a compound of Formula XXXIII and thereafter the product is treated with hydrazine or methylamine in substantially the same manner as in STEP E to afford a compound of Formula XXXIV.

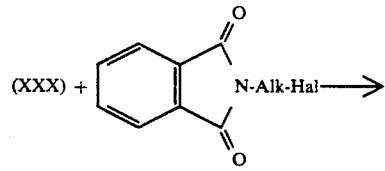

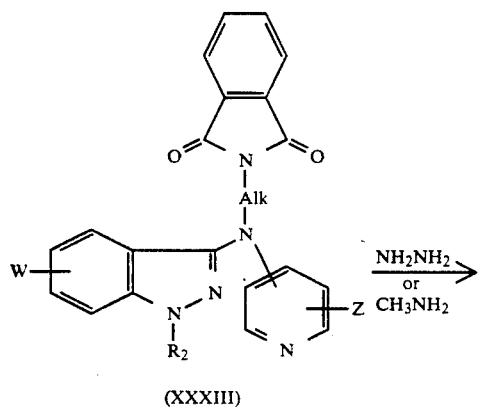

Compound XXX is allowed to react with a compound of the formula Hal-Alk-Hal to afford a compound of Formula XXXV and the product is allowed to react with a compound of the formula R'NH$_2$ in substantially the same manner as in STEP E to afford a compound of Formula XXXVI.

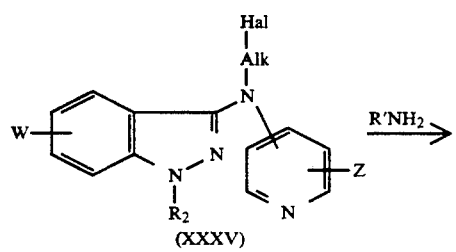

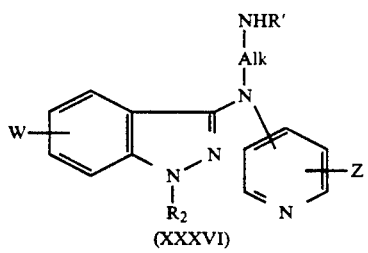

STEP N

Compound XXX is allowed to react with an acid halide of the formula $$R_9-\overset{O}{\underset{\|}{C}}-Hal$$

in substantially the same manner as in STEP F to afford a compound of formula XXXVII.

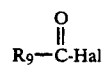

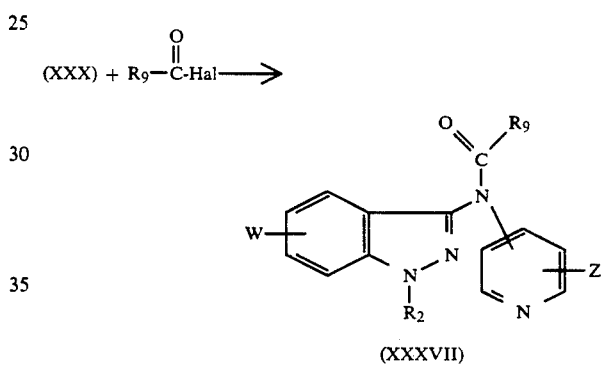

Compound XXX is allowed to react with a compound of the formula $$RO-\overset{O}{\underset{\|}{C}}-NH-Alk-\overset{O}{\underset{\|}{C}}-Hal$$

to afford a compound of Formula XXXVIII and thereafter the product is hydrolyzed in substantially the same manner as in STEP F to afford a compound of Formula XXXIX.

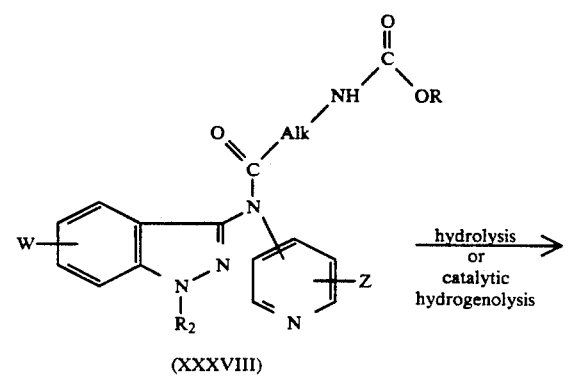

-continued

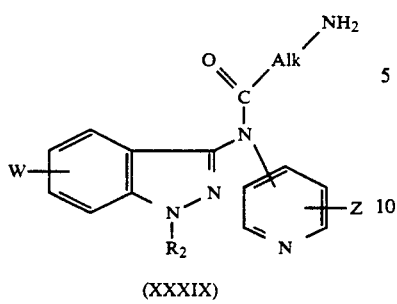

(XXXIX)

Compound XXX is allowed to react with compound XIX in the presence of dicyclohexylcarbodiimide in substantially the same manner as in STEP F to afford compound XXXVIII.

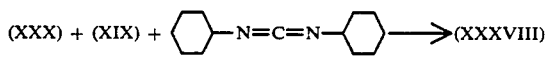

In the foregoing description of synthetic steps, where a compound in which the group —Z is —$NH_2$ is desired, it can be prepared by reducing the corresponding compound in which the group —Z is —$NO_2$ with a suitable reducing agent such as zinc and hydrochloric acid or catalytically with a hydrogen and a suitable noble metal catalyst such as palladium or platinum in a routine manner known to the art.

The compounds of Formula I of the present invention are useful for the treatment of various memory dysfunctions such as Alzheimer's disease, as modulators of neurotransmitter function such as serotonergic and adrenergic, and as such are useful as antidepressants, anxiolytics, atypical antipsychotics, antiemetics, and for the treatment of personality disorders such as obsessive compulsive disorders.

[$^3$H]-8-Hydroxy-2-(di-n-propylamino)tetralin ([$^3$H]DPAT) Binding to Serotonin (5HT$_{1A}$) Receptors Purpose The purpose of this assay is to determine the affinity of test compounds for the 5HT$_{1A}$ receptor in brain. It is believed to be useful for predicting compounds with serotonergic properties with potential utility as novel anxiolytics, atypical antipsychotics or useful for the treatment of personality disorders such as obsessive compulsive disorder.

Introduction

The existence of two populations of 5HT receptors in rat brain was shown by differential sensitivity to spiroperidol (1). The spiroperidol-sensitive receptors were designated as the 5HT$_{1A}$ subtype and the insensitive receptors were referred to as the 5HT$_{1B}$ subtype (2). Other 5HT binding sites (5HT$_{1C}$, 5HT$_{1D}$ and 5HT$_3$) have subsequently been identified in various species, based on differential sensitivity to 5HT antagonists (3). A significant advance in the classification of 5HT receptors came with the identification of a selective ligand for the 5HT$_{1A}$ receptor, [$^3$H]DPAT (4). These authors reported that [$^3$H]DPAT labeled an autoreceptor. Lesion studies suggest that [$^3$H]DPAT labeled receptors are not terminal autoreceptors, but may be somatodendritic autoreceptors (5). Although DPAT decreases the firing rate in the Raphe nucleus and inhibits 5HT release, the actual location and function is somewhat controversial (6). These studies and the sensitivity of [$^3$H]DPAT binding to guanine nucleotides and effects on adenylate cyclase suggest that DPAT acts as an agonist at the 5HT$_{1A}$ receptor (7).

Procedure I

A. Reagents

1. Tris Buffers, pH 7.7
   (a) 57.2 g Tris HCl
   16.2 g Tris base
   Bring volume to 1 liter with distilled water
   (0.5M Tris buffer, pH 7.7, buffer 1a).
   (b) Make a 1:10 dilution in deionized $H_2O$ (0.05M Tris buffer, pH 7.7, buffer 1b).
   (c) 0.05M Tris buffer, pH 7.7 containing 10 $\mu$M pargyline, 4 mM $CaCl_2$ and 0.1% ascorbic acid (buffer 1c).
   0.49 mg pargyline·HCl
   111 mg $CaCl_2$
   250 mg ascorbic acid
   Bring to 250 ml with 0.05M Tris buffer, pH 7.7 (reagent 1b)
2. 8-Hydroxy[$^3$H]-DPAT (2-(N,N-Di[2,3(n)-$^3$H]propylamino-8-hydroxy-1,2,3,4-tetrahydronaphthalene) (160–206 Ci/mmol) was obtained from Amersham.
   For IC$_{50}$ determinations: a 10 nM stock solution is made up and 50 $\mu$l added to each tube (final concentration=0.5 nM).
3. Serotonin creatinine sulfate. 0.5 mM stock solution is made up in 0.01N HCl and 20 $\mu$l added to 3 tubes for determination of nonspecific binding (final concentration=10 $\mu$M).
4. Test Compounds. For most assays, a 1 mM stock solution is made up in a suitable solvent and serially diluted, such that the final concentration in the assay ranges from $2 \times 10^{-5}$ to $2 \times 10^{-8}$M. Seven concentrations are used for each assay. Higher or lower concentrations may be used based on the potency of the drug.

B. Tissue Preparation

Male Wistar rats are sacrificed by decapitation. Hippocampi are removed, weighed and homogenized in 20 volumes of 0.05M Tris buffer, pH 7.7. The homogenate is centrifuged at 48,000 g for 10 minutes and the supernatant is discarded. The pellet is resuspended in an equal volume of 0.05M Tris buffer, incubated at 37° C. for 10 minutes and recentrifuged at 48,000 g for 10 minutes. The final membrane pellet is resuspended in 0.05M Tris buffer containing 4 mM $CaCl_2$, 0.1% ascorbic acid and 10 $\mu$M pargyline.

C. Assay

800 $\mu$l Tissue
130 $\mu$l 0.05M Tris+$CaCl_2$+pargyline+ascorbic acid
20 $\mu$l vehicle/5HT/drug
50 $\mu$l [$^3$H]DPAT Tubes are incubated for 15 minutes at 25° C. The assay is stopped by vacuum filtration through Whatman GF/B filters which are then washed 2 times with 5 ml of ice-cold 0.05M Tris buffer. The filters are then placed into scintillation vials with 10 ml of Liquiscint scintillation cocktail and counted.

Calculation

Specific binding is defined as the difference between total binding and binding in the presence of 10 μM 5HT. $IC_{50}$ values are calculated from the percent specific binding at each drug concentration.

Procedure II

A. Reagents

1. Tris Buffers, pH 7.7
   (a) 57.2 g Tris HCl
   16.2 g Tris base
   Bring to 1 liter with distilled water
   (0.5M Tris buffer, pH 7.7, buffer 1a).
   (b) Make a 1:10 dilution in distilled H₂O (0.05M Tris buffer,
   pH 7.7 at 25° C., buffer 1b).
   (c) 0.05M Tris buffer, pH 7.7 containing 10 μM pargyline, 4 mM CaCl₂ and 0.1% ascorbic acid (buffer 1c).
   0.49 mg pargyline·HCl
   110.99 mg CaCl₂
   250 mg ascorbic acid
   Bring to 250 ml with 0.05M Tris buffer, pH 7.7 (buffer 1b).
2. 8-Hydroxy[$^3$H]-DPAT (2-N,N-Di[2,3(n)-$^3$H]propylamino)-[8-hydroxy-1,2,3,4-tetrahydronaphthalene)] (160–206 Ci/mmol) is obtained from Amersham.

For $IC_{50}$ determinations: $^3$H-DPAT is made up to a concentration of 3.3 nM in the Tris Buffer (1c) such that when 150 μl is added to each tube a final concentration of 0.5 nM is attained in the 1 ml assay.

3. Serotonin creatinine sulfate is obtained from the Sigma Chemical Company. Serotonin creatinine sulfate is made up to a concentration of 100 μM in Tris buffer (1c). One hundred μl is added to each of 3 tubes for the determination of nonspecific binding (this yields a final concentration of 10 μM in the 1 ml assay).

4. Test Compounds. For most assays, a 100 μM stock solution is made up in a suitable solvent and serially diluted with Tris buffer (1c) such that when 100 μl of drug is combined with the total 1 ml assay, a final concentration ranging from $10^{-5}$ to $10^{-8}$M is attained. Characteristically seven concentrations are studied for each assay; however, higher or lower concentrations may be used, depending on the potency of the drug.

B. Tissue Preparation

Male Wistar rats are decapitated, the hippocampi are removed and homogenized in 20 volumes of ice cold 0.05M Tris buffer, pH 7.7 (1b). The homogenate is centrifuged at 48,000 g for 10 minutes at 4° C. The resulting pellet is rehomogenized in fresh Tris buffer (1b), incubated at 37° C. for 10 minutes and recentrifuged at 48,000 g for 10 minutes. The final membrane pellet is resuspended in 0.05M Tris buffer (1c) containing 4 mM CaCl₂, 0.1% ascorbic acid and 10 μM pargyline. Specific binding is approximately 90% of total bound ligand.

C. Assay

750 μl Tissue
150 μl [$^3$H]DPAT
100 μl vehicle (for total binding) or 100 μM serotonin creatinine sulfate (for nonspecific binding) or appropriate drug concentration Tubes are incubated for 15 minutes at 25° C. The assay is stopped by vacuum filtration through Whatman GF/B filters which are then washed 2 times with 5 ml of ice-cold 0.05M Tris buffer (1b). The filters are then placed into scintilltion vials with 10 ml of Liquiscint scintillation cocktail and counted. Specific binding is defined as the difference between total binding in the absence or presence of 10 μM serotonin creatinine sulfate. $IC_{50}$ values are calculated from the percent specific binding at each drug concentration.

The $K_D$ value for [$^3$H] DPAT binding was found to be 1.3 nM by Scatchard analysis of a receptor saturation experiment. The $K_i$ value may then be calculated by the Cheng-Prusoff equation:

$$K_i = IC_{50}/1 + L/K_D$$

References

1. Pedigo, N. W., Yammamura, H. I. and Nelson, D. L.: Discrimination of multiple [$^3$H]5-hydroxytryptamine binding sites by the neuroleptic spiperone in rat brain. J. Neurochem. 36: 220–226 (1981).
2. Middlemiss, D. N. and Fozard J. R.: 8-Hydroxy-2-(di-n-propylamino)tetralin discriminates between subtypes of the 5HT₁ recognition site. Eur. J. Pharmacol. 90: 151–152 (1983).
3. Peroutka, S. J.: Pharmacological differentiation and characterization of 5-HT$_{1A}$, 5-HT$_{1B}$ and 5-HT$_{1C}$ binding sites in rat frontal cortex. J. Neurochem. 47: 529–540 (1986).
4. Peroutka, S. J.: 5-Hydroxytryptamine receptor subtypes: molecular, biochemical and physiological characterization TINS 11: 496–500 (1988).
5. Gozlan, H., El Mestikawy, S., Pichat, L. Glowinsky, J. and Hamon, M.: Identification of presynaptic serotonin autoreceptors using a new ligand: $^3$H-DPAT. Nature 305: 140–142 (1983).
6. Verge, D., Daval, G., Marcinkiewicz, M., Patey, A., El Mestikawy, H. Gozlan and Hamon, M.: Quantitative autoradiography of multiple 5-HT₁ receptor subtypes in the brain of control or 5,7,dihydroxytryptamine-treated rats. J. Neurosci. 6: 3474–3482 (1986).
7. Schlegel, R. and Peroutka, S. J.: Nucleotide interactions with 5-HT$_{1A}$ binding sites directly labeled by [$^3$H]-8-hydroxy-2-(di-n-propylamino)tetralin ([$^3$H]-8-OH-DPAT). Biochem. Pharmacol. 35: 1943–1949 (1986).
8. Dourish C. T., Hutson, P. H. and Curzon, G.: Putative anxiolytics 8-OH-DPAT, buspirone and TVX Q 7821 are agonists at 5 HT$_{1A}$ autoreceptors in the raphe nucleus. TIPS 7: 212–214 (1986).
9. Iversen, S. D.: 5HT and anxiety. Neuropharmacol. 23: 1553–1560 (1984).
10. Traber J. and Glaser, T.: 5HT$_{1A}$ receptor-related anxiolytics. TIPS 8: 432–437 (1987).
11. Peroutka, S. J.: Selective interaction of novel anxiolytics with 5-hydroxytryptamine$_{1A}$ receptors. Biol. Psychiatry. 20: 971–979 (1985).

$^3$H-GR 65630 Binding to Rat Entorhinal Cortex Membranes: 5HT₃ Receptor Binding Assay

Purpose

The purpose of this assay is to determine the affinity of test compounds for the 5HT₃ binding site in the brain. This is believed to be useful for predicting the potential of compounds to exhibit antiemetic, anxiolytic or atypical antipsychotic profiles.

Introduction

Presently, it is generally accepted that there are three different receptor subtypes for the neurotransmitter serotonin (5HT); $5HT_1$, $5HT_2$ and $5HT_3$. The $5HT_1$ and $5HT_2$ binding sites have been well characterized and further subdivided based on data from binding and functional activity studies (1,2). The $5HT_3$ binding site, on the other hand, has only recently begun to be characterized. Originally it was believed that $5HT_3$ binding sites existed only in the periphery (3). However, with the recent introduction of potent and selective $5HT_3$ antagonist drugs such as GR65630, zacopride, ICS 205 930 and MDL 72222, data from binding studies have indicated that $5HT_3$ binding sites are also located in select areas of the brain (4,5,6). The highest levels of $5HT_3$ binding sites have been detected in limbic and dopamine containing brain areas (entorhinal cortex, amygdala, nucleus accumbens and tuberculum olfactorium) (4). Besides possessing selective binding in dopamine rich areas, $5HT_3$ antagonists have been reported to block behavioral effects associated with certain drugs of abuse (nicotine and morphine) and to be active in behavioral tests predictive of anxiolytic activity. Based on these selective regional binding results and behavioral studies, it has been speculated that $5HT_3$ antagonists may have a therapeutic benefit in disease states believed to be associated with excessive dopaminergic activity; e.g., schizophrenia and drug abuse.

Procedure

A. Reagents 1. 0.05M Krebs-Hepes buffer, pH 7.4
11.92 g Hepes
10.52 g NaCl
0.373 g KCl
0.277 g $CaCl_2$
0.244 g $MgCl_2 \cdot 6H_2O$
Bring to 1 liter with distilled $H_2O$.
Bring pH up to 7.4 (at 4° C.) with 5N NaOH.

2. [$^3$H]-GR65630 (87.0 Ci/mmol) is obtained from New England Nuclear. For $IC_{50}$ determinations: [$^3$H]-GR65630 is made up to a concentration of 1.0 nM in Krebs-Hepes buffer such that when 100 μl is added to each tube a final concentration of 0.4 nM is attained in the 250 μl assay.

3. Zacopride maleate is obtained from Research Biochemicals Inc. Zacopride maleate is made up to a concentration of 500 μM in Krebs-Hepes buffer. 50 μl is added to each of 3 tubes for the determination of nonspecific binding (yields a final concentration of 100 μM in the 250 μl assay).

4. Test Compounds: For most assays, a 50 μM stock solution is made up in a suitable solvent and serially diluted with Krebs-Hepes buffer such that when 50 μl of drug is combined with the total 250 μl assay, a final concentration from $10^{-5}$ to $10^{-8}$ is attained. Characteristically seven concentrations are studied for each assay; however, higher or lower concentrations may be used, depending on the potency of the drug.

B. Tissue Preparation

Male Wistar rats (150–200 g) are decapitated, the entorhinal cortex removed, weighed and homogenized in 10 volumes of ice-cold 0.05M Krebs-Hepes buffer, pH 7.4. The homogenate is centrifuged at 48,000 g for 15 minutes at 4° C. The resulting pellet is rehomogenized in fresh Krebs-Hepes buffer and recentrifuged at 48,000 g for 15 minutes at 4° C. The final pellet is resuspended in the original volume of ice-cold Krebs-Hepes buffer. This yields a final tissue concentration of 1.2–1.6 mg/ml with the addition of 100 μl to the assay. Specific binding is approximately 55–65% of total bound ligand.

C. Assay

100 μl Tissue suspension
100 μl [$^3$H]-GR65630
50 μl Vehicle (for total binding) or 500 μM Zacopride maleate (for nonspecific binding) or appropriate drug concentration Sample tubes are kept on ice for additions, then vortexed and incubated with continuous shaking for 30 minutes at 37° C. At the end of the incubation period, the incubate is diluted with 5 ml of ice-cold Krebs-Hepes buffer and immediately vacuum filtered through Whatman GF/B filters, followed by two 5-ml washes with ice-cold Krebs-Hepes buffer. The filters are dried and counted in 10 ml of liquid scintillation cocktail. Specific GR65630 binding is defined as the difference between the total binding and that bound in the presence of 100 μM Zacopride. $IC_{50}$ calculations are performed using computer-derived log-probit analysis.

References

1. Peroutka, S. J. 5-Hydroxytryptamine receptor subtypes: Molecular biochemical and physiological characterization. Trends In Neuroscience 11: 496–500 (1988).

2. Watling, K. J. $5HT_3$ receptor agonists and antagonists. Neurotransmission 3: 1–4 (1989).

3. Costell, B., Naylor, R. J. and Tyers, M. B. Recent advances in the neuropharmacology of $5HT_3$ agonists and antagonists. Rev. Neuroscience 2: 41–65 (1988).

4. Kilpatrick, G. J., Jones, B. P. and Tyers, M. B. Identification and distribution of $5HT_3$ receptors in rat brain using radioligand binding. Nature 330: 746–748 (1987).

5. Barnes, N. M., Costell, B. and Naylor, R. J. [$^3$H] Zacopride: Ligand for the identification of $5HT_3$ recognition sites. J. Pharm. Pharmacol. 40: 548–551 (1988).

6. Watling, K. J., Aspley, S., Swain, C. J. and Saunders, J. [$^3$H] Quaternised ICS 205-930 labels $5HT_3$ receptor binding sites in rat brain. Eur. J. Pharmacol. 149: 397–398 (1988).

$^3$H-Serotonin Uptake in Rat Whole Brain Synaptosomes

Purpose

This assay is used as a biochemical screen for compounds which block serotonin (5HT) uptake, which may be useful as antidepressants and for the treatment of personality disorders such as obsessive compulsive disorder.

Introduction

Asberg and coworkers have suggested that subjects with serotonergic hypofunction comprise a biochemical subgroup of depressed patients (1), while others (2) claim that altered serotonergic function determines the mood changes associated with affective disorders. Although the role of 5HT in the etiology of depression is not clear; it is true that a number of antidepressant drugs block the 5HT reuptake mechanism. In vitro receptor binding assays have shown that [$^3$H]-imipramine labels 5HT uptakes sites (10). Trazodone and zimelidine are clinically effective antidepressants (3) with fairly selective effects on 5HT uptake (4,5). More recently, fluoxetine has been shown to be both a selective and potent 5HT uptake inhibitor.

[$^3$H]-5HT transport has been characterized in CNS tissue (6,7) and found to be saturable, sodium- and temperature-dependent, inhibited by ouabain, metabolic inhibitors, tryptamine analogs (8) and tricyclic antidepressants (tertiary amines>>secondary amines) (9). The latter findings differentiate 5HT uptake from catecholamine uptake. [$^3$H]-5HT uptake can also be used as a marker for serotonin nerve terminals.

Procedure

A. Animals: Male CR Wistar rats (100-125 g).

B. Reagents

1. Krebs-Henseleit Bicarbonate Buffer, pH 7.4 (KHBB): Make a 1 liter batch, containing the following salts.

|  | g/L | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |
| Prior to use add: |  |  |
| Dextrose | 2 mg/ml | 11.1 |
| Iproniazid phosphate | 0.30 mg/ml | 0.1 |

Aerate for 60 min. with 95% O$_2$/5% CO$_2$, check pH (7.4±0.1)

2. 0.32M Sucrose: 21.9 g of sucrose, bring to 200 ml.

3. Serotonin creatinine SO$_4$ is obtained from Sigma Chemical Co. A 0.1 mM stock solution is made up in 0.01N HCl. This is used to dilute the specific activity of radiolabeled 5HT.

4. 5-[1,2-$^3$H(N)]-Hydroxytryptamine creatinine sulfate (Serotonin), specific activity 20-30 Ci/mmol is obtained from New England Nuclear.

The final desired concentration of $^3$H-5HT in the assay is 50 nM. The dilution factor is 0.8. Therefore, the KHBB is made up to contain 62.5 nM [$^3$H]-5HT.

Add to 100 ml of KHBB.

| A | 56.1 µl of 0.1 mM 5HT = | 56.1 nM |
|---|---|---|
| *B | 0.64 nmole of $^3$H-5HT = | 6.4 nM |
|  |  | 62.5 nM |

*Calculate volume added from specific activity of $^3$H-5HT.

5. For most assays, a 1 mM solution of the test compound is made up in suitable solvent and serially diluted such that the final concentration in the assay ranges from 2×10$^{-8}$ to 2×10$^{-5}$M. Seven concentrations are used for each assay. Higher or lower concentrations may be used depending on the potency of the compound.

C. Tissue Preparation

Male Wistar rats are decapitated and the brain rapidly removed. Whole brain minus cerebella is weighed and homogenized in 9 volumes of ice-cold 0.32M sucrose using a Potter-Elvejhem homogenizer. Homogenization should be done with 4-5 up and down strokes at medium speeds to minimize synaptosome lysis. The homogenate is centrifuged at 1000 g for 10 min. at 0°-4° C. The supernatant (S$_1$) is decanted and is used for uptake experiments.

D. Assay

800 µl KHBB+[$^3$H]-5HT

20 µl Vehicle or appropriate drug concentration

200 µl Tissue suspension Tubes are incubated at 37° C. under a 95% O$_2$/5% CO$_2$ atmosphere for 5 minutes. For each assay, 3 tubes are incubated with 20 µl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. IC$_{50}$ values are derived from log-probit analysis.

References:

1. Asberg, M., Thoren, P., Traskman, L., Bertilsson, L., and Ringberger, V. "Serotonin depression: -A biochemical subgroup within the affective disorders. Science 191: 478-480 (1975).
2. DeMontigy, C. Enhancement of 5 HT neurotransmission by antidepressant treatments. J. Physiol. (Paris) 77:455-461 (1980).
3. Feighner, J. P. Clinical efficacy of the newer antidepressants. J. Clin. Psychopharmacol. 1:235-265 (1981).
4. Ogren, S. O., Ross, S. B., Hall, H., Holm, A. C. and Renyi, A. L. The pharmacology of zimelidine: A 5HT selective reuptake inhibitor. Acta Psychiat. Scand. 290: 127-151 (1981).
5. Clements-Jewry, S., Robson, P. A. and Chidley, L. J. Biochemical investigations into the mode of action of trazodone. Neuropharmacol. 19: 1165-1173 (1980).
6. Ross, S. B. Neuronal transport of 5-hydroxytryptamine. Pharmacol. 21: 123-131 (1980).
7. Shaskan, E. G. and Snyder, S. H. Kinetics of serotonin accumulation into slices from rat brain: Relationship to catecholamine uptake. J. Pharmacol. Exp. Ther. 175: 404-418 (1970).
8. Horn, S. A. Stucture activity relations for the inhibition of 5HT uptake into rat hypothalamic homogenates by serotonin and tryptamine analogues. J. Neurochem. 21: 883-888 (1973).
9. Horn, A. S. and Trace, R.C.A.M. Structure-activity relations for the inhibition of 5-hydroxytryptamine uptake by tricyclic antidepressant into synaptosomes from serotonergic neurones in rat brain homogenates. Brit. J. Pharmacol. 51: 399-403 (1974).
10. Langer, S. Z., Moret, C., Raisman, R., Dubocovich, M. L. and Briley M. High affinity [$^3$H]imipramine binding in rat hypothalamus: Association with uptake of serotonin but not norepinephrine. Science 210: 1133-1135 (1980).

Results of the three assay methods described above are presented in Table 1 for a representative compound of this invention.

TABLE 1

| Compound | 5HT$_{1A}$ Receptor Binding IC$_{50}$ ($\mu$M) | 5HT$_3$ Receptor Binding IC$_{50}$ ($\mu$M) | Inhibition of $^3$H-serotonin Uptake IC$_{50}$ ($\mu$M) |
|---|---|---|---|
| 3-(4-pyridinylamino)-1H-indole | 6.4 | 5.5 | 14.6 |
| Buspirone | 0.062 | | >20 |
| MDL 72222 | | 0.53 | |
| Clozapine | 0.58 | 1.02 | >20 |
| Chloripramine | | | 0.15 |
| Amitriptyline | | | 0.83 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
3-(4-pyridinylamino)-1H-indole;
N-(1H-indol-3-yl)-N-(4-pyridinyl)propanamide;
3-(4-pyridinylamino)benzo[b]thiophene;
N-(benzo[b]thiophen-3-yl)-N-(4-pyridinyl)propanamide;
3-(3-fluoro-4-pyridinylamino)-1H-indole;
3-(propyl-4-pyridinylamino)-1H-indole;
1-methyl-3-(4-pyridinylamino)-1H-indole;
6-fluoro-3-(4-pyridinylamino)benzo[b]thiophene;
5-phenylmethoxy-3-(4-pyridinylamino)-1H-indole;
5-hydroxy-3-(4-pyridinylamino)-1H-indole;
6-fluoro-3-(propyl-4-pyridinylamino)benzo[b]thiophene;
3-(4-pyridinylamino)benzo[b]thiophene;
3-(4-pyridinylamino)-1H-indol-5-yl methylcarbamate;
3-(4-pyridinylamino)-1H-indol-5-yl benzylcarbamate;
3-[N-propyl-N-(3-fluoro-4-pyridinyl)amino]-1H-indol-5-yl benzylcarbamate;
3-[N-propyl-N-(3-fluoro-4-pyridinyl)amino]-1H-indole;
3-(4-pyridinylamino)-1H-indazole;
3-[N-propyl-N-(4-pyridinyl)amino]-1H-indazole;
1-methyl-3-(4-pyridinylamino)-1H-indazole;
1-methyl-3-(propyl-4-pyridinyl)amino-1H-indazole;
2-amino-N-(1H-indol-3-yl)-N-(4-pyridinyl)acetamide;
2-amino-N-(1-methyl-1H-indol-3-yl)-N-(4-pyridinyl)acetamide;
2-amino-N-(1-methyl-1H-indazol-3-yl)-N-(4-pyridinyl)acetamide;
2-amino-N-(1H-indazol-3-yl)-N-(4-pyridinyl)acetamide; and
2-amino-N-(benzo[b]thiophen-3-yl)-N-(4-pyridinyl)acetamide;

The following examples are presented in order to illustrate the present invention.

EXAMPLE 1

3-(4-Pyridinylamino)-1H-indole maleate

A solution of 3-aminoindole (8 g) and 4-chloropyridine hydrochloride (12 g) in 150 mL 1-methyl-2-pyrrolidinone was stirred at 70°-75° C. for one hour, after which additional 4-chloropyridine hydrochloride (4 g) was added. After stirring a total of two hours, the mixture was cooled, stirred with water, basified with sodium carbonate and extracted with ethyl acetate. The organic extract was washed successively with water and a saturated sodium chloride solution and thereafter dried (anhydrous magnesium sulfate), filtered and concentrated to 20 g of a dark oil. This was eluted through silica with 20% methanol in dichloromethane via HPLC (high performance liquid chromatography) yield 7 g of dark oil. This oil was crystallized from acetonitrile to yield 3 g light brown crystals, m.p. 192°–193°. A 2.8 g portion was converted to the maleate salt in 50% methanol/ether to yield 3.5 g of light tan crystals, m.p. 149°–151° C. Recrystallization from 50% methanol/ether yielded 3.4 g of light tan crystals, m.p. 149°–151° C.

ANALYSIS: Calculated for $C_{17}H_{15}N_3O_4$: 62.76% C; 4.65% H; 12.92% N; Found: 62.85% C; 4.70% H; 12.92% N.

EXAMPLE 2

N-(1H-Indol-3-yl)-N-(4-pyridinyl)propanamide 3-(4-Pyridinylamino)-1H-indole (3 g) was added to a solution prepared from propionic anhydride (3 g), 10 mL dichloromethane and 10 mL toluene. The resultant solution was stirred one hour at ambient temperature and thereafter stirred with water and basified with sodium carbonate. The product was extracted into dichloromethane. The dried (anhydrous magnesium sulfate) organic layer was filtered and concentrated. The residue was eluted through silica with 50% ethyl acetate in dichloromethane via flash column chromatography to yield 3.5 g of a light tan solid, m.p. 166°–168°. A 1.5 g portion was recrystallized from acetonitrile to yield 1.3 g of light tan crystals, m.p. 168°–170°.

ANALYSIS: Calculated for $C_{16}H_{15}N_3O$: 72.43% C; 5.70% H; 15.84% N; Found: 72.06% C; 5.69% H; 15.94% N.

EXAMPLE 3

3-(3-Fluoro-4-pyridinylamino)-1H-indole hydrochloride

A solution of 3-aminoindole (7 g) and 4-chloro-3-fluoropyridine hydrochloride (13 g) in 200 mL of 1-methyl-2-pyrrolidinone was stirred at 75°–80° C. for two hours, after which additional 4-chloro-3-fluoropyridine hydrochloride (5 g) was added. After stirring a total of three hours the mixture was cooled, stirred with water, basified with sodium carbonate and extracted with ethyl acetate. The dried (anhydrous magnesium sulfate) organic layer was filtered and concentrated to 20 g of a dark oil. Elution through silica gel first with dichloromethane and then with 50% ethyl acetate in dichloromethane via flash column chromatography yielded 17 g of a dark oil. This oil was eluted through silica with ether via flash column chromatography to yield 10.6 g of a dark oil. This oil was eluted through silica with 20% ethyl acetate in dichloromethane via HPLC to yield 8 g of a dark oil. A six gram portion was converted to the hydrochloride salt in methanol/ether to yield 3.5 g of a solid, m.p. >250° C. Recrystallization from 30% methanol in ether yielded 2.7 g of crystals, m.p. 256°–258° C. (dec.).

ANALYSIS: Calculated for $C_{13}H_{11}ClFN_3$: 59.21% C; 4.20% H; 15.93% N; Found: 59.06% C; 4.14% H; 15.49% N.

EXAMPLE 4

6-Fluoro-3-(4-pyridinylamino)benzo[b]thiophene maleate

A solution of 3-amino-6-fluorobenzo[b]thiophene (7 g) and 4-chloropyridine hydrochloride (7 g) in 200 mL 1-methyl-2-pyrrolidinone was stirred one hour at 80°–85° C. and thereafter cooled, stirred with water, basified with sodium carbonate and extracted with ethyl acetate. The organic extract was washed successively with water and a saturated sodium chloride solution and thereafter dried (anhydrous magnesium sulfate), filtered and concentrated to 10 g of a dark oil. This oil was eluted through silica with 10% methanol in dichloromethane via HPLC to yield 4.7 g of a brown solid, m.p. 102°–106° C. This was converted to the maleate salt in 20% methanol in ether and immediately thereafter recrystallized from 20% methanol in ether to yield 2.9 g of white crystals, m.p. 172°–174° (dec.).

ANALYSIS: Calculated for $C_{17}H_{13}FN_2O_4S$: 56.66% C; 3.64% H; 7.78% N; Found: 56.41% C; 3.44% H; 7.68% N.

EXAMPLE 5

6-Fluoro-3-(propyl-4-pyridinylamino)benzo[b]thiophene hydrochloride

A solution of 6-fluoro-3-(4-pyridinylamino)benzo[b]thiophene (4.2 g) in 20 mL of dimethylformamide was slowly added to a suspension of sodium hydride (0.42 g) in 5 mL of dimethylformamide. Following the anion formation, a solution of 1-bromopropane (2.3 g) in 10 mL of dimethylformamide was added. After one hour the reaction mixture was stirred with water and extracted with ethyl acetate. The organic extract was washed successively with water and a saturated sodium chloride solution, and thereafter dried (anhydrous magnesium sulfate), filtered, and concentrated to 5 g of a dark oil. This oil was eluted through silica gel with ethyl acetate via flash column chromatography to yield 3.3 g of a yellow oil. This oil was converted to the hydrochloride salt in 20% methanol in ether to yield 3.3 g of yellow crystals, m.p. 290°–292° C. (dec.).

ANALYSIS: Calculated for $C_{16}H_{16}ClFN_2S$: 59.53% C; 5.00% H; 8.68% N; Found: 59.16% C; 5.00% H; 8.26% N.

We claim:

1. A compound of the formula

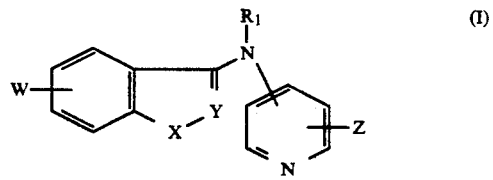

(I)

where $R_1$ is hydrogen, loweralkyl, loweralkenyl, loweralkynyl, arylloweralkyl, aminoloweralkyl, loweralkylaminoloweralkyl, formyl, loweralkylcarbonyl, aminoloweralkylcarbonyl or loweralkoxycarbonyl; the group —X—Y= is

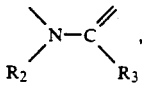

, $R_2$ and $R_3$ being independently hydrogen or loweralkyl;

W is hydrogen, halogen, hydroxy, loweralkoxy, arylloweralkoxy or

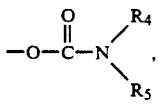

where $R_4$ is hydrogen, loweralkyl or arylloweralkyl; $R_5$ is loweralkyl or arylloweralkyl;

and Z is hydrogen, halogen, loweralkyl, nitro or amino; the term aryl in each occurrence signifying a phenyl group substituted with 0, 1 or 2 substituents each of which being independently loweralkyl, loweralkoxy, halogen or trifluomethyl; or a pharmaceutically acceptable acid addition salt thereof.

2. The compound as defined in claim 1, which is 3-(4-pyridinylamino)-1H-indole.

3. The compound as defined in claim 1, which is N-(1H-indol-3-yl)-N-(4-pyridinyl)propanamide.

4. The compound as defined in claim 1, which is 3-(3-fluoro-4-pyridinylamino)-1H-indole.

5. The compound as defined in claim 1, which is 3-(propyl-4-pyridinylamino)-1H-indole.

6. The compound as defined in claim 1, which is 1-methyl-3-(4-pyridinylamino)-1H-indole.

7. The compound as defined in claim 1, which is 5-phenylmethoxy-3-(4-pyridinylamino)-1H-indole.

8. The compound as defined in claim 1, which is 5-hydroxy-3-(4-pyridinylamino)-1H-indole.

9. The compound as defined in claim 1, which is 3-(4-pyridinylamino)-1H-indol-5-yl methylcarbamate.

10. The compound as defined in claim 1, which is 3-(4-pyridinylamino)-1H-indol-5-yl benzylcarbamate.

11. The compound as defined in claim 1, which is 3-[N-propyl-N-(3-fluoro-4-pyridinyl)amino]-1H-indol-5-yl benzylcarbamate.

12. The compound as defined in claim 1, which is 3-[N-propyl-N-(3-fluoro-4-pyridinyl)amino]-1H-indole.

13. The compound as defined in claim 1, which is 2-amino-N-(1H-indol-3-yl)-N-(4-pyridinyl)acetamide and which can be depicted as

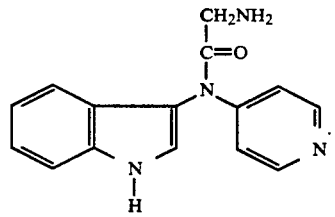

14. The compound as defined in claim 1, which is 2-amino-N-(1-methyl-1H-indol-3-yl)-N-(4-pyridinyl)acetamide and which can be depicted as

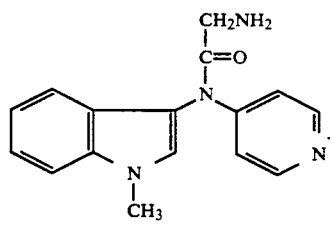

15. A pharmaceutical composition which comprises a compound as defined in claim 1 in an amount effective for alleviating a memory dysfunction and a suitable carrier therefor.

* * * * *